(12) United States Patent
Ko et al.

(10) Patent No.: US 11,241,277 B2
(45) Date of Patent: Feb. 8, 2022

(54) SKIN TREATMENT APPARATUS USING RF ENERGY AND METHOD FOR SKIN TREATMENT USING SAME

(71) Applicant: LUTRONIC CORPORATION, Goyang (KR)

(72) Inventors: Kwang Chon Ko, Paju (KR); Richard Howard Cohen, San Rafael, CA (US)

(73) Assignee: LUTRONIC CORPORATION, Goyang (KR)

( * ) Notice: Subject to any disclaimer, the term of this patent is extended or adjusted under 35 U.S.C. 154(b) by 840 days.

(21) Appl. No.: 16/041,375

(22) Filed: Jul. 20, 2018

(65) Prior Publication Data

US 2019/0059992 A1  Feb. 28, 2019

(30) Foreign Application Priority Data

Aug. 25, 2017 (KR) .................. 10-2017-0107942

(51) Int. Cl.
 *A61B 18/14* (2006.01)
 *A61B 18/12* (2006.01)
 *A61B 18/00* (2006.01)

(52) U.S. Cl.
CPC ...... *A61B 18/1477* (2013.01); *A61B 18/1206* (2013.01); *A61B 18/14* (2013.01);
(Continued)

(58) Field of Classification Search
CPC . A61B 18/1206; A61B 18/14; A61B 18/1477; A61B 2018/0016; A61B 2018/00452; A61B 2018/0047; A61B 2018/00702; A61B 2018/00761; A61B 2018/00875; A61B 2018/00958; A61B 2018/1273; A61B 2018/143; A61B 2018/1495
See application file for complete search history.

(56) References Cited

U.S. PATENT DOCUMENTS

2008/0183167 A1   7/2008  Alexander et al.
2009/0299361 A1*  12/2009  Flyash .................. A61B 18/18
                                                        606/33
(Continued)

FOREIGN PATENT DOCUMENTS

JP    2004520852 A   7/2004
KR    20100014365 A  2/2010
(Continued)

*Primary Examiner* — Michael F Peffley

(57) ABSTRACT

Disclosed herein are a skin treatment apparatus using RF energy and a skin treatment method using the same. There are provided a skin treatment apparatus using RF energy, including a first handpiece configured to include a first electrode unit coming into contact with a skin surface and to form perforations through which an agent penetrates by transferring RF energy to the skin surface through the first electrode unit, a second handpiece configured to include a second electrode unit inserted into the inside of the skin and to insert the second electrode unit into the inside of the skin into which the agent has penetrated and transfer the RF energy, and a controller configured to control parameters of the RF energy transferred to the first electrode unit and the second electrode unit, and a treatment method using the same.

7 Claims, 15 Drawing Sheets

(52) U.S. Cl.
CPC ............... *A61B 2018/0016* (2013.01); *A61B 2018/0047* (2013.01); *A61B 2018/00452* (2013.01); *A61B 2018/00702* (2013.01); *A61B 2018/00761* (2013.01); *A61B 2018/00875* (2013.01); *A61B 2018/00958* (2013.01); *A61B 2018/1273* (2013.01); *A61B 2018/143* (2013.01); *A61B 2018/1495* (2013.01)

(56) References Cited

U.S. PATENT DOCUMENTS

| | | | |
|---|---|---|---|
| 2014/0005658 A1* | 1/2014 | Rosenbegr | A61B 18/18 606/33 |
| 2014/0155963 A1* | 6/2014 | Ko | A61N 5/00 607/101 |
| 2014/0194789 A1* | 7/2014 | Ko | A61B 5/6848 601/18 |
| 2014/0358200 A1* | 12/2014 | Ko | A61N 1/328 607/101 |
| 2017/0209695 A1* | 7/2017 | Solomon | A61B 18/203 |

FOREIGN PATENT DOCUMENTS

| | | |
|---|---|---|
| KR | 20130009511 A | 1/2013 |
| KR | 20160038566 A | 4/2016 |
| KR | 20170019024 A | 2/2017 |
| KR | 20170086461 A | 7/2017 |
| WO | 0132232 A2 | 5/2001 |
| WO | 2013012204 A2 | 1/2013 |
| WO | 2016052893 A1 | 4/2016 |

* cited by examiner

SKIN TREATMENT APPARATUS USING RF ENERGY AND METHOD FOR SKIN TREATMENT USING SAME

CROSS-REFERENCE TO RELATED APPLICATIONS

Priority to Korean patent application number 10-2017-0107942 filed on Aug. 25, 2017, the entire disclosure of which is incorporated by reference herein, is claimed.

BACKGROUND OF THE INVENTION

Field of the Invention

The present invention relates to a skin treatment apparatus using radio frequency (RF) energy and a skin treatment method using the same and, more particularly, to a skin treatment apparatus using a combination of various types of electrodes and a skin treatment method using the same.

Discussion of the Related Art

Recently technologies for treating the skin by modifying the state of a skin tissue by transferring energy to the skin or improving tissue characteristics are widely applied. Skin treatment apparatuses using various energy sources, such as a laser, a flash lamp and ultrasonic waves, are developed. Active research is recently carried out on a skin treatment apparatus using RF energy.

When RF energy is supplied to a skin tissue, an RF current flows into the skin tissue. In this case, the skin tissue functions as resistance, so deep heat occurs in the skin tissue. The deep heat raises a temperature of the skin tissue to reorganize the collagen layer, thus being capable of improving wrinkle and enhancing skin elasticity. Furthermore, there are effects in that skin aging can be prevented and an overall skin state can be improved by increasing the blood circulation of the skin tissue.

A skin treatment apparatus using an RF is divided into a contact type in which an electrode transfers RF energy in the state in which the electrode has touched a skin surface and an invasive type in which RF energy is transferred to the inside of the skin in the state in which the electrode has been inserted into the skin. In general, a lesion occurring in a skin surface is treated using the electrode of the contact type and a lesion occurring within a skin tissue is treated using the invasive type. In this case, a conventional treatment apparatus using RF energy includes an individual treatment apparatus depending on such a treatment type, so there is a need for a treatment method using a combination of the contact type and the invasive type.

SUMMARY OF THE INVENTION

Embodiments of the present invention propose a treatment apparatus and treatment method using RF energy, which can improve a treatment effect by combining a contact type treatment type and an invasive type treatment type in a treatment apparatus and treatment method using RF energy.

In an aspect, there is provided a skin treatment apparatus using radio frequency (RF) wave energy, including a first handpiece configured to include a first electrode unit coming into contact with a skin surface and to form perforations through which an agent penetrates by transferring RF energy to the skin surface through the first electrode unit, a second handpiece configured to include a second electrode unit inserted into the inside of the skin and to insert the second electrode unit into the inside of the skin into which the agent has penetrated and transfer the RF energy, and a controller configured to control parameters of the RF energy transferred to the first electrode unit and the second electrode unit.

In this case, the agent may include an anesthesia component in order to alleviate pain occurring when the second electrode unit is inserted when treatment using the second handpiece is performed.

Furthermore, the first handpiece selectively operates in a first mode in which perforations are formed in the skin surface or a second mode in which RF energy for lesion treatment on a skin surface is transferred without forming perforations in the skin surface. The controller may control the parameters of the RF energy transferred to the first electrode unit based on an operating mode of the first handpiece. In this case, the RF energy transferred to the skin surface through the first electrode unit has a waveform of a pulse form, and an RF energy waveform of the first mode is controlled to have a larger peak power value or shorter pulse width than an RF energy waveform of the second mode.

Meanwhile, the second handpiece may operate in various treatment modes based on an insertion depth of the second electrode unit or an RF energy parameter transferred through the second electrode unit. The controller may control the parameters of the RF energy of the first handpiece based on a set treatment mode of the second handpiece.

For example, as the insertion depth of the second electrode unit or an amount of the RF energy transferred through the second electrode unit is increased, the controller may control to increase output of the RF energy transferred through the first electrode unit of the first handpiece so that the agent easily penetrates the skin.

Furthermore, the skin treatment apparatus according to an embodiment of the present invention may further include a notification unit configured to notify a user of a treatment time using the second handpiece. The notification unit may be configured to notify the user of a treatment time using the second handpiece when a preset time elapses from the treatment start time of the first handpiece, the treatment end time of the first handpiece or a time set by the user.

Furthermore, the controller may determine the transfer end time of the RF energy by sensing impedance of the skin surface when the perforations are formed in the skin surface using the first handpiece. Specifically, the controller may determine that perforations have been formed in the section in which the impedance of the skin surface suddenly rises while the perforations are formed in the skin surface using the first handpiece, and may control to terminate the transfer of the RF energy.

Furthermore, an embodiment of the present invention may also provide a skin treatment method using radio frequency (RF) wave energy, including a perforation forming step of forming perforations in a skin surface by transferring RF energy to the skin surface using a first handpiece including a first electrode unit coming into contact with the skin surface, a step of applying an agent to the skin surface in which the perforations have been formed, and a treatment step of treating the skin by transferring RF energy to the inside of the skin into which the agent has penetrated using a second handpiece including a second electrode unit inserted into the inside of the skin.

<Description of reference numerals>

| | |
|---|---|
| 100: main body | 130: RF generator |
| 160: controller | 200: first handpiece |
| 220: first electrode unit | 300: second handpiece |
| 350: second electrode unit | |

DETAILED DESCRIPTION OF THE EMBODIMENTS

Hereinafter, a skin treatment apparatus according to embodiments of the present invention is described in detail with reference to the drawings. In the following description, the location relations between elements are described in principle based on the drawings. Furthermore, the drawings may be enlarged and shown in order to simplify the structure of the invention for convenience of description or if necessary. Accordingly, the present invention is not limited thereto, and various devices may be added, changed or omitted.

Hereinafter, the "treatment apparatus" includes all apparatuses for treating mammals including people. The treatment apparatus may include may include various treatment apparatuses used to improve a lesion or the state of a tissue. For example, the treatment apparatus includes an apparatus transferring treating substances, such as medicines, anesthetic, and stem cells, an operation apparatus for surgically treating a specific tissue, and various treatment apparatuses transferring RF energy.

Hereinafter, a "tissue" means a set of cells forming various body organs of an animal including people, and includes various tissues forming various organs within the body, including a skin tissue.

Figure 1:
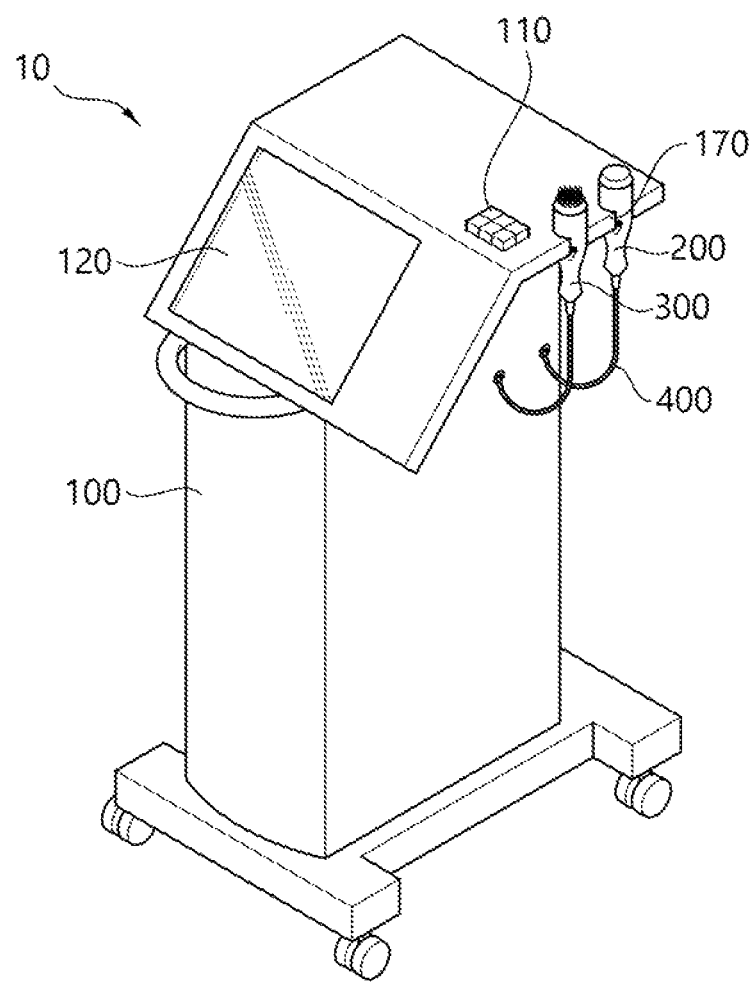
FIG. 1 is a perspective view showing a skin treatment apparatus using RF energy according to an embodiment of the present invention.

FIG. 1 is a perspective view showing a skin treatment apparatus using RF energy according to an embodiment of the present invention. As shown in FIG. 1, the RF skin treatment apparatus 10 includes a main body 100, and a first handpiece 200 and second handpiece 300 detachably installed on the main body.

The main body 100 forms a body that forms a major frame of the skin treatment apparatus. The main body 100 is equipped with a power supply (not shown) supplied with external power. A control panel 110 configured to manipulate the operation contents of the treatment apparatus and a display 120 configured to display the operation contents for a user may be positioned on an external surface of the main body (in FIG. 1, the control panel has been illustrated as being an element separated from the display, but the control panel and the display may be integrated to form a touch screen panel). An RF generator 130 configured to generate RF energy using power from the power supply is positioned within the main body 100. RF energy generated from the RF generator 130 is selectively supplied to the first handpiece 200 and the second handpiece 300. Cradles 170 in which the first handpiece 200 and the second handpiece 300 are respectively held may be provided on an external surface of the main body.

The first handpiece 200 and the second handpiece 300 are configured to include respective bodies 210 and 310 and respective electrode units 220 and 350. Each of the bodies 210 and 310 forms the frame of each handpiece and is configured to enable a user to grasp it when the user performs a surgical procedure. Manipulation units 211 and 311 configured to enable a user to manipulate the operation contents of each handpiece during a surgical procedure may be formed on an external surface of the body. The electrode units 220 and 350 of the first handpiece and the second handpiece are provided at the ends of the bodies, respectively. Each electrode unit receives RF energy from the RF generator 130 of the main body and transfers it to a skin tissue. In this case, the first electrode unit 220 of the first handpiece and the second electrode unit 350 of the second handpiece have different shapes, and are described in detail later.

The first handpiece 200 and the second handpiece 300 may be connected to the main body 100 by cables 400. An RF transmitter 402 configured to transmit RF energy and a signal line 401 may be included in each of the cables 400. The RF transmitter 402 forms a transmission circuit for transferring RF energy to the skin by electrically connecting the RF generator 130 of the main body to each of the electrode units 220 and 350 of the handpieces. The signal lines 401 transmit various control signals or sensing signals between the main body 100 and the handpieces 200 and 300. For example, the signal lines 401 transmit control signals manipulated by a user through the manipulation units 211 and 311 of the respective handpieces and sensing signals sensed by the sensors 212 and 346 of the respective handpieces to the controller 160 of the main body. Alternatively, when the controller 160 of the main body 100 generates control signals to control the operations of the respective handpieces, the control signals may be transferred to the handpieces through the signal lines 401.

As shown in FIG. 1, the two cables 400 are extended and formed in the main body 100. The first handpiece 200 and the second handpiece 300 are positioned at the ends of the respective cables. The first handpiece 200 and the second handpiece 300 may maintain the state in which they are always connected to the main body. A user may select the first handpiece 200 and the second handpiece 300 held in the cradles 170 and perform a surgical procedure. The treatment apparatus of the present embodiment has been illustrated as having the two handpieces, but may include various handpieces. Furthermore, the first handpiece and the second handpiece are not always connected, but the first handpiece and the second handpiece may be alternately coupled and used.

Figure 2:
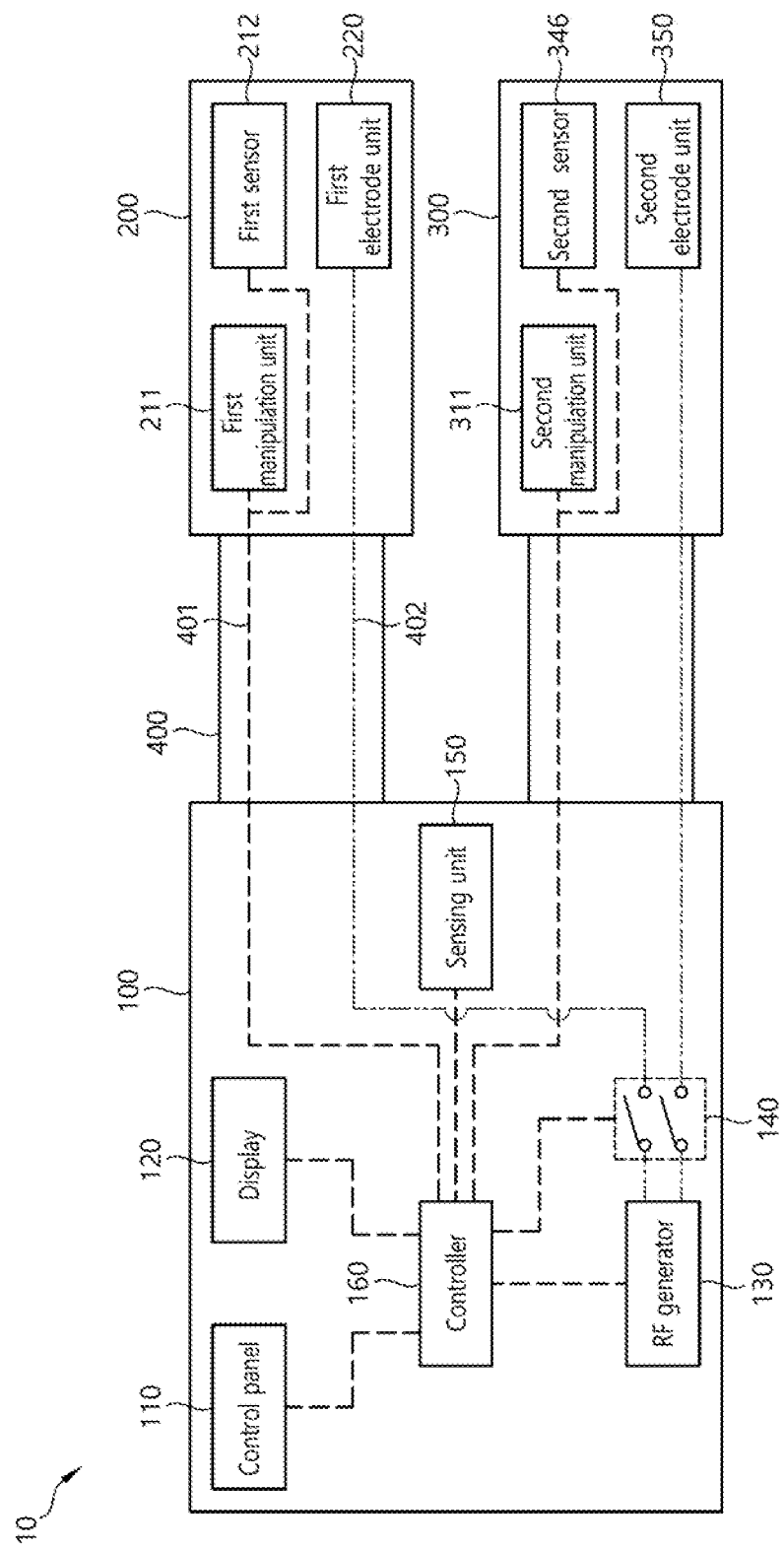
FIG. 2 is a block diagram schematically showing the configuration of the skin treatment apparatus of FIG. 1.

FIG. 2 is a block diagram schematically showing the configuration of the skin treatment apparatus of FIG. 1. As shown in FIG. 2, various elements, including the control panel 110 configured to enable a user to set an operating mode of the treatment apparatus, the display 120 configured to display a variety of types of information including the operation contents of the treatment apparatus for a user, and the RF generator 130 configured to generate RF energy, are disposed in the main body 100. The RF generator 130 is electrically connected to the first and second handpieces 200 and 300 and may transmit RF energy to the electrode units 220 and 350. Operations of the various elements may be controlled by the controller 160.

For example, when a user sets an operating mode through the control panel 110, information about the corresponding mode is transferred to the controller 160. The controller 160 controls whether the RF generator will operate, an RF transmission path 140, etc. so that an operation corresponding to the set mode is performed. Accordingly, RF energy is transferred to the electrode unit of the first handpiece 200 or the second handpiece 300, so treatment may be performed. The parameters of RF energy transferred to the handpieces may be differently controlled depending on the type of handpiece, treatment contents, etc. because the first handpiece 200 and the second handpiece 300 have different treatment objects, different treatment locations and/or different electrode forms. Furthermore, the controller 160 may display operation contents and information, sensed by various sensors, while the treatment apparatus operates on the display 120 for a user.

The treatment apparatus according to an embodiment of the present invention may further include a sensing unit 150 configured to sense the type of handpiece to be used by a user. When a user picks up one of the first and second handpieces held in the cradles from the cradles, the sensing unit 150 may be configured to sense such picking up. For example, the sensing unit may be provided in each of the bodies of the first and second handpieces. When a user grasps one of the first and second handpieces, the sensing unit may be configured to sense such a grasp. Information sensed by the sensing unit 150 is transferred to the controller 160. The controller 160 may determine whether a suitable handpiece corresponding to a mode set by a user is used. If it is determined that a wrong handpiece is used, the controller 160 may notify the user of such a fact. The notification method may be any one of a voice method, a visual method and a haptic method. For example, each of the bodies of the first and second handpieces may include a haptic notification unit (not shown) for generating vibration. A user may be notified of the use of a wrong handpiece through the haptic notification unit.

Figure 3:
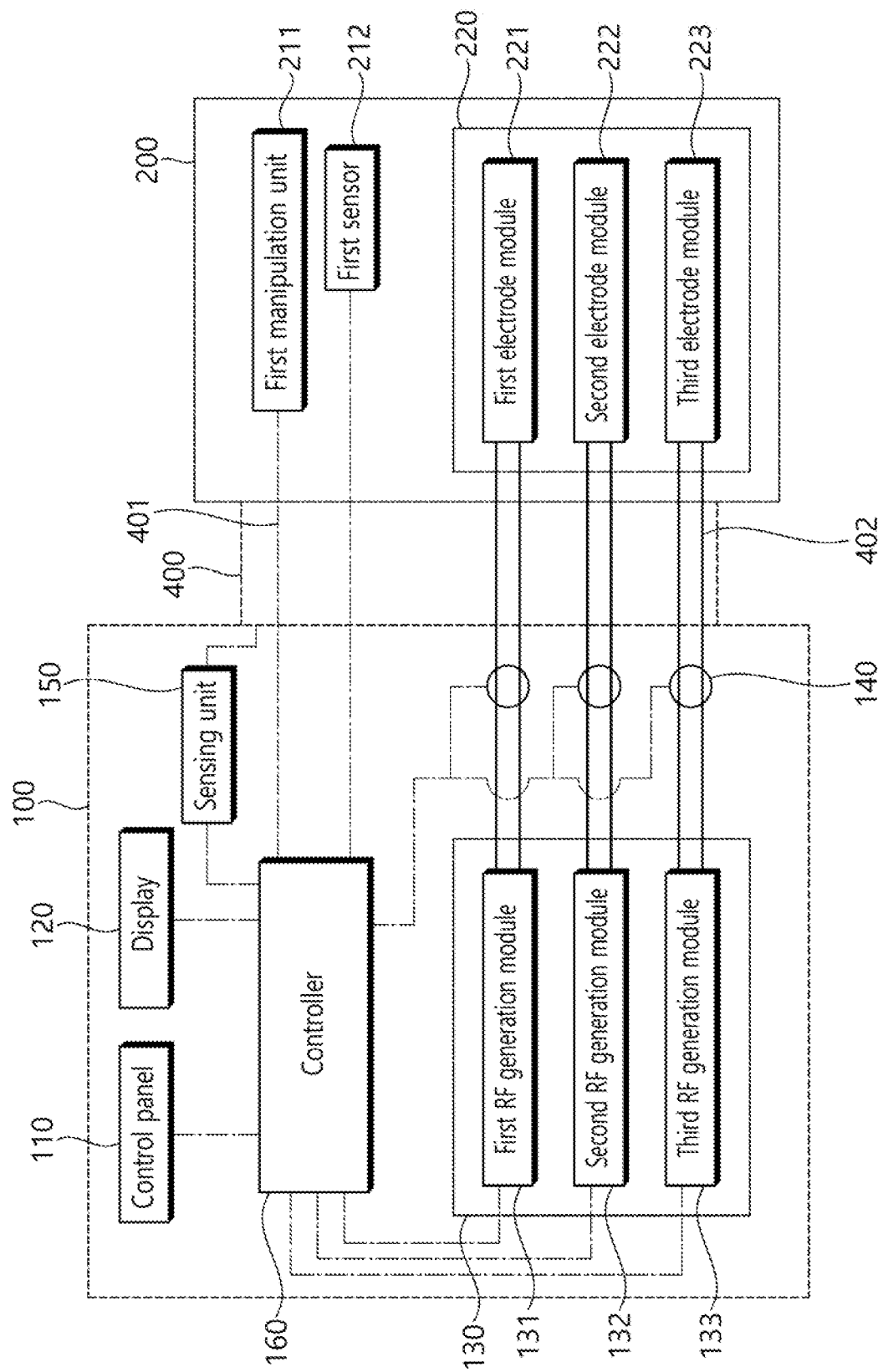
FIG. 3 is a block diagram schematically showing the configuration of a first handpiece of FIG. 1.
Figure 4:
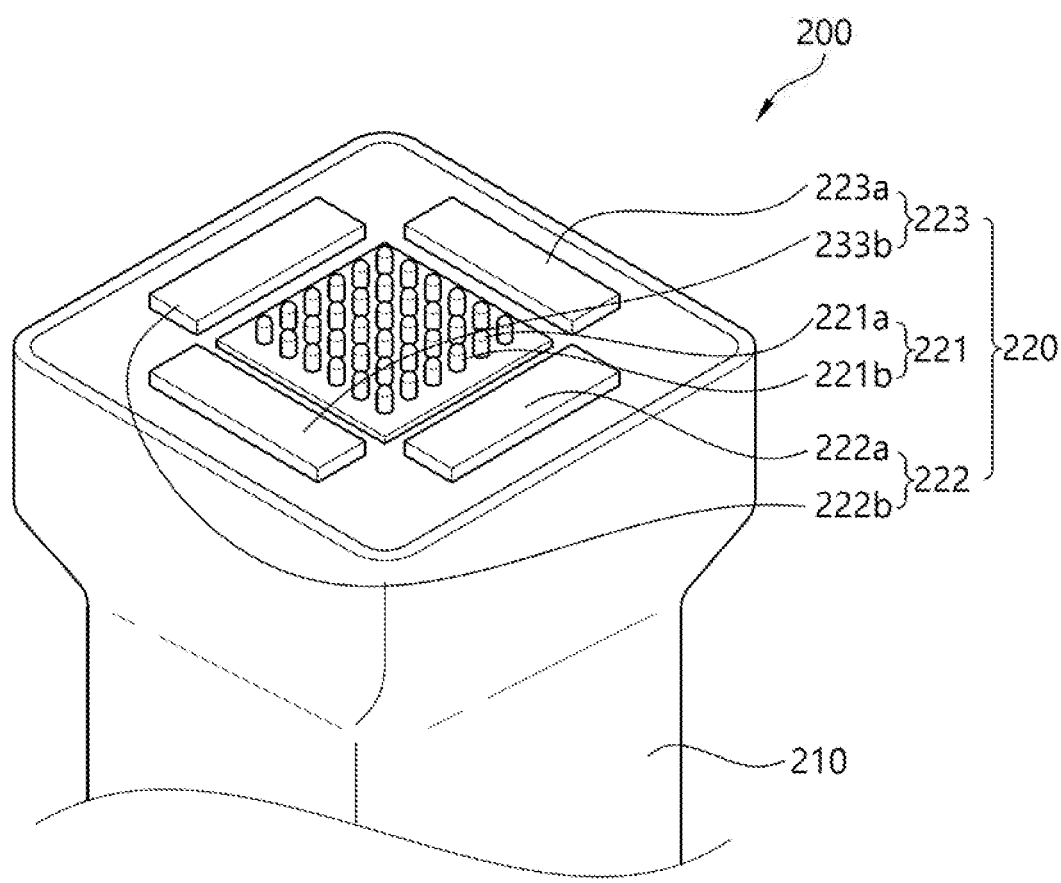
FIG. 4 is a perspective view showing a shape of the end of the first handpiece of FIG. 1.

FIG. 3 is a block diagram schematically showing the configuration of the first handpiece of FIG. 1 (connection relations between the elements of the first handpiece in FIG. 2 are chiefly shown). FIG. 4 is a perspective view showing a shape of the end of the first handpiece of FIG. 1. Hereinafter, the configuration of the first handpiece is described more specifically with reference to FIGS. 3 and 4.

As shown in FIG. 3, the first manipulation unit 211 configured to enable a user to control the operation of the first handpiece is formed an external surface of the body of the first handpiece 200. Furthermore, the first electrode unit 220 configured to transmit RF energy to a skin surface by coming into contact with the skin surface is formed at the end of the first handpiece 200.

As shown in FIG. 4, the first electrode unit 220 may include multiple electrode modules 221, 222 and 223. Each electrode module is configured to include at least one positive electrode and at least one negative electrode. For example, the first electrode unit 220 may be configured to include the first electrode module 221, and the second electrode module 222 and the third electrode module 223 disposed on the outside of the first electrode module (refer to FIG. 4). Each electrode module is protruded and formed at the end of the first handpiece and configured to come into contact with the skin. Specifically, the first electrode module 221 is configured to include a plurality of protruded electrodes, each one having an end of a round shape, so that point contacts are performed at a plurality of spots on a surface of the skin. Each of the second electrode module 222 and the third electrode module 223 may be configured to have an end of a curved surface or flat surface so that it comes into surface contact with the skin in a specific area or more upon treatment. For example, the area that the second electrode module 222 or the third electrode module 223 comes into contact with the skin may be 20 times or more the area that one protruded electrode 221 of the first electrode module 221 comes into contact with the skin.

Specifically, the first electrode module 221 has a structure in which protruded electrodes 221a forming multiple positive electrodes and protruded electrodes 221b forming multiple negative electrodes have been disposed in a support plate 351 (refer to FIG. 6) having a specific area and a square or oblong plate shape. Furthermore, in the second electrode module 222 and the third electrode module 223, positive electrodes 222a and 223a and negative electrodes 222b and 223b are disposed on both sides so that they face each other with the first electrode module 221 interposed between the second electrode module 222 and the third electrode module 223. In this case, the direction in which the positive electrode and negative electrode of the second electrode module 222 are disposed may be orthogonal to the direction in which the positive electrode and negative electrode of the third electrode module 223 are disposed (e.g., the second electrode module may be positioned on the left and right sides of the first electrode module, and the third electrode module may be positioned on the upper and lower sides of the second electrode module).

In the first electrode module to the third electrode module, RF energy from the RF generator of the main body 100 may be transferred through independent paths. In this case, the RF generator 130 includes a plurality of RF generation modules (e.g., first to third RF generation modules 131, 132 and 133) as lower elements. The first to third electrode modules may receive RF energy from respective RF generation modules. Accordingly, the controller may independently control the parameters of the RF energy transferred to the skin through the electrode modules by controlling the respective RF generation modules and the respective RF transmission paths 140, or may control the parameters of the RF energy so that RF energy is transferred through only some electrode modules.

Furthermore, the first handpiece 200 may include the first sensor 212 configured to sense the state in which the first electrode unit 220 has touched the skin. The first sensor 212 may include an impedance sensor or a pressure sensor positioned at the end of the body of the first handpiece 200. Alternatively, the first sensor 212 may be configured to determine whether a touch is present based on information of current flowing through a corresponding electrode using some electrodes forming the first electrode unit 220.

Contact state information sensed by the first sensor 212 is transferred to the controller 160. If the first sensor 212 senses that contact state information of the first electrode unit 220 is poor, the controller 160 may generate a contact failure signal and notify a user of the contact failure signal through the display or a separate warning sound.

Figure 5:
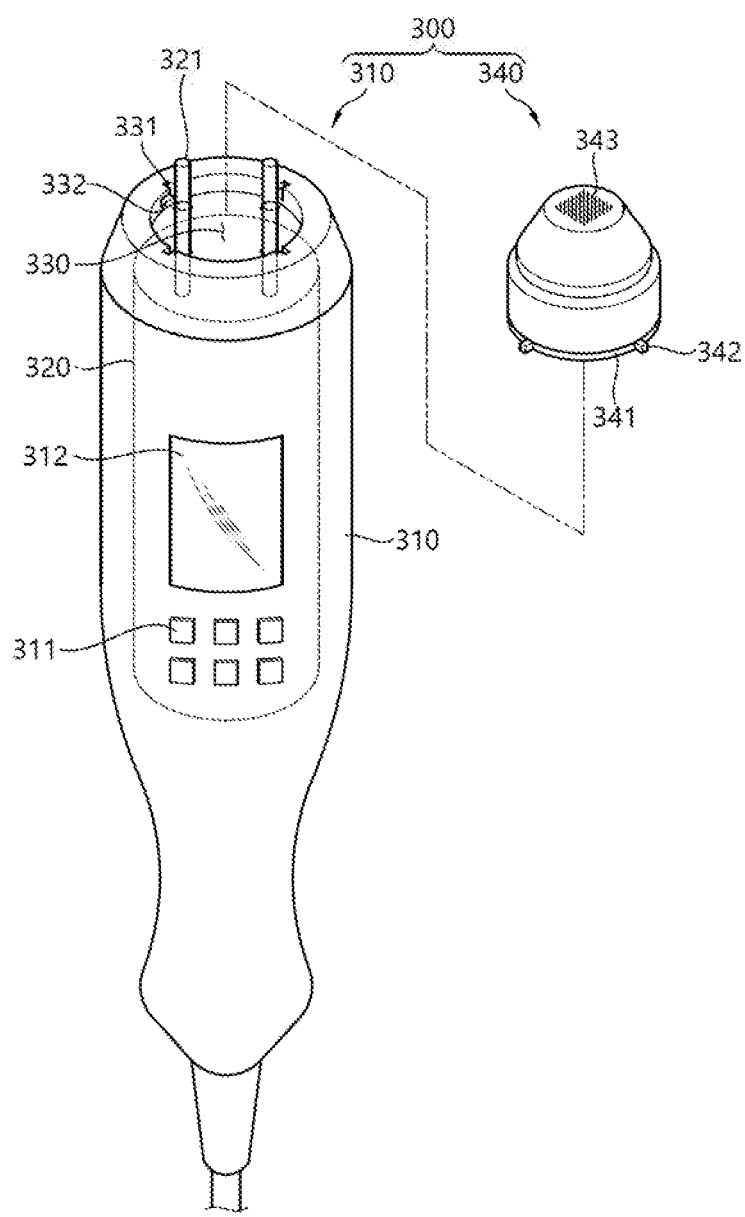
FIG. 5 is a perspective view schematically showing the configuration of a second handpiece of FIG. 1.
Figure 6:
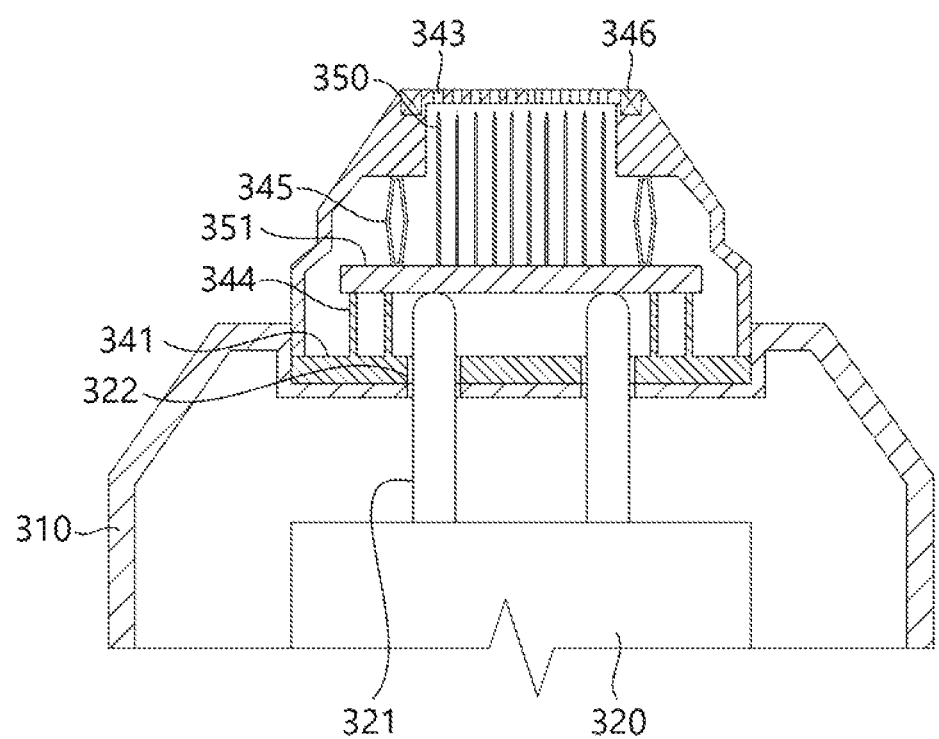
FIG. 6 is a cross-sectional view showing a shape of the end of the second handpiece of FIG. 1.

FIG. 5 is a perspective view schematically showing the configuration of the second handpiece of FIG. 1. FIG. 6 is a cross-sectional view showing a shape of the end of the second handpiece of FIG. 1. Hereinafter, the configuration of the second handpiece is described more specifically with reference to FIGS. 5 and 6.

As shown in FIG. 5, the second handpiece 300 includes a second manipulation unit 311 enabling a user to control the operation of the second handpiece. Furthermore, the second electrode unit 350 inserted into the inside of the skin to transmit RF energy is formed at the end of the second handpiece 300. The second electrode unit 350 is moved by a driving unit 320 provided within the body of the second handpiece, and is inserted into the inside of the skin through a skin surface.

As shown in FIG. 5, the second electrode unit 350 includes a plurality of micro needles 350, each one having a sharp end, so that they can be easily inserted into a skin tissue. The micro needle according to an embodiment of the present invention may have a diameter in the range of several to several thousands of μm. For example, a needle having a diameter in the range of 10 to 1000 μm may be used. The micro needles 350 are electrically connected to the RF generator 130, and transmit RF energy to the inside of the skin. A surface of the body of the micro needle 350 except the end to which RF energy is transferred is made of an insulating material. Accordingly, the second electrode unit 350 may transmit RF energy to a local area where the end of the micro needle is positioned in the state in which the second electrode unit 350 has been inserted into the skin.

The driving unit 320 of the second handpiece 300 is configured to linearly move an output terminal 321 provided at one end of the handpiece in the length direction. When the output terminal 321 linearly moves, the plurality of needles 350 disposed at the end of the output terminal advances and retracts to and from a contact surface of the handpiece (i.e., a surface at the end of the body of the second handpiece that neighbors a skin surface of a patient when treatment is performed). Accordingly, the second electrode unit 350 can be inserted into the inside of the skin of the patient or drawn out from the inside of the skin by the driving of the driving unit 320. The driving unit 320 may include a solenoid, a linear actuator using a hydraulic/pneumatic cylinder, etc.

The second manipulation unit 311 may control the on/off of the second handpiece 300, the insertion depth of the second electrode unit 350, or the amount of energy transferred through the second electrode unit 350. Furthermore, a separate display unit 312 is provided on an external surface of the second handpiece 300. The display unit 312 may display a variety of types of information necessary during treatment for a user. Accordingly, the user can manipulate treatment contents through the second manipulation unit and check treatment contents through the display unit 312 in the state in which the user has grasped the second handpiece by a hand.

The second electrode unit 350 includes the plurality of micro needles, and may include a tip module 340 detachably positioned at the end of the second handpiece 300. Specifically, a base 341 forms the bottom of the tip module 340. Detachment protrusions 342 that are outward protruded are formed on the outer wall of the base 341. Guide grooves 331 configured to guide the detachment protrusions 342 and an anti-separation groove 332 configured to prevent the detachment protrusions guided along the guide grooves from being detached are formed in a recess unit 330 to which the tip module 340 is coupled on the side of the second handpiece 300. The tip module 340 may be positioned in the second handpiece 300 in such a manner that the detachment protrusions 342 of the tip module 340 are guided along the guide grooves 331 and coupled to the anti-separation groove 332. In this case, in addition to the aforementioned coupling structure, the detachment protrusions 342 may be detachably disposed using various other coupling structures, and the tip module may be integrated with the second handpiece.

The end of the second handpiece 300 where the tip module 340 is positioned is a portion where treatment is performed through a touch with a skin tissue. The support plate 351 in which the plurality of needles 350 is disposed is provided within the tip module 340. The plurality of needles 350 is fixed and disposed in the support plate 351 in a matrix form. RF energy is transferred to the needles through a circuit formed in the support plate 351. The front surface of the tip module may form a portion that neighbors or comes into contact with the skin of a patient when treatment is performed. A plurality of through holes 343 through which the plurality of needles advances and retracts is formed in the front surface of the tip module.

At least one hole 322 through which the output terminal 321 can pass is formed at the bottom of the tip module 340. The output terminal 321 pressurizes the support plate 351 while linearly moving through the hole 322 when the driving unit operates. The back of the support plate 351 is seated in a support 344 positioned within the tip module, and the front thereof is pressurized by an elastic member 345 positioned within the tip module 340. When the output terminal 321 moves and pressurizes the support plate 351, the support plate 351 detaches from the support and advances, so the plurality of micro needles 350 is protruded toward the front of the through holes 343 and inserted into a skin tissue. Furthermore, when the output terminal is retracted by the driving of the driving unit 320, the support plate is retracted by the restoring force of the elastic member 345, so the plurality of needles also returns to the inside of the tip module.

Although not specifically shown in the drawing, the circuit of the support plate 351 is configured to be electrically connected to the RF generator 130 when the tip module 340 is coupled to the end of the second handpiece. Alternatively, the circuit of the support plate may be configured to be selectively electrically connected to the RF generator 130 when the support plate is pressurized by the output terminal (e.g., an electrode may be formed at the end of the output terminal and electrically connected to the support plate when the support plate is pressurized).

The second handpiece 300 is used in such a manner that a user drives the second manipulation unit 311 in the state in which the user has positioned the end of the second handpiece on the skin. When the driving unit 320 is driven by a manipulation of the second manipulation unit 311, the micro needles 350 of the tip module are advanced and inserted into the inside of the skin. Furthermore, when RF energy is transferred to a target location in the state in which the micro needles 350 have been inserted and the transfer of the RF energy is completed, the micro needles 350 are retracted by the driving of the driving unit 320. The advancing operation, RF energy transfer, and retracting operation of the second electrode unit may be performed as a series of consecutive operations.

Furthermore, the second handpiece may be configured to have a second sensor 346 at its end and to sense a variety of types of information during a treatment operation. For example, like the first sensor, the second sensor 346 may be configured to include an impedance sensor or a pressure sensor and to sense whether the skin has been touched or a pressurization state. Alternatively, the second sensor 346 may be configured to include a displacement sensor or a location sensor and to sense skin surface displacement when the micro needles are inserted. Alternatively, the second sensor 346 may be configured to include an impedance sensor and to measure impedance of a skin tissue during invasive treatment. In this case, the controller 160 may control elements by incorporating information sensed by the second sensor 346 or notify a user whether the treatment apparatus is normal during a treatment operation using the sensed information.

As described above, the RF treatment apparatus 10 according to an embodiment of the present invention is configured to include the first handpiece configured to transmit RF energy using the skin touch method and the second handpiece configured to transmit RF energy using the skin insertion method. Accordingly, the RF treatment apparatus can perform treatment according to a method of transferring RF energy using a handpiece suitable for a skin lesion of a patient.

Hereinafter, a method of controlling the treatment apparatus and treatment method according to a treatment lesion are described more specifically.

Figure 7:
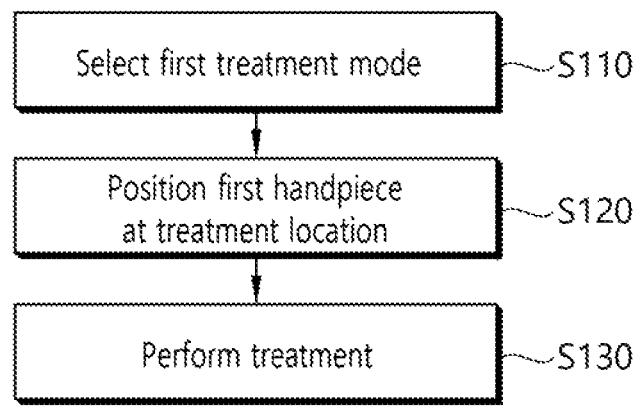
FIG. 7 is a flowchart showing treatment steps using a first treatment method.

FIG. 7 is a flowchart showing treatment steps using a first treatment method. The first treatment method is a treatment mode performed according to a method of transferring RF energy to a skin surface. The first treatment method is applied to treat a wide pore, fine wrinkles, etc. and is used to perform treatment using the first handpiece 200.

As shown in FIG. 7, when a user selects the first treatment mode using the control panel 110 or the display 120 (S110), the controller switches the mode of the first handpiece 200 into an available mode so that treatment can be performed using the first handpiece. In this step, the controller 160 controls the RF generator 130 to generate RF energy of parameters corresponding to set treatment contents. Furthermore, the controller controls the RF transmission path 140 along which RF energy is transferred so that the generated RF energy is transferred to the first handpiece.

When the user selects the treatment mode, the user positions the first handpiece 200 at a treatment location by holding the first handpiece (S120). In this step, the first electrode unit 220 of the first handpiece may be positioned to touch a skin surface. At this time, if the controller 160 detects that the user tries to use a handpiece (e.g., the second handpiece in this step) different from the handpiece of the selected mode based on a signal sensed by the sensing unit 150, the controller may generate an abnormal signal and notify the user of the abnormal signal.

Thereafter, the user manipulates the first manipulation unit 211 so that RF energy is transferred to the skin surface through the first electrode unit 220, and performs treatment (S130). In the present embodiment, the first manipulation unit 211 configured to drive the first handpiece may be provided in the body of the first handpiece 200 or may be configured using a pedal that the user steps on using a foot.

While this step is performed, the first electrode module 221, second electrode module 222 and third electrode module 223 of the first electrode unit 220 transmit the RF energy to the skin surface at the same time or in a preset sequence. To this end, the controller 160 controls the first to third RF energy generation modules of the RF generator 130 to operate so that RF energy of a preset pattern is transferred to the electrode modules.

Figure 8:
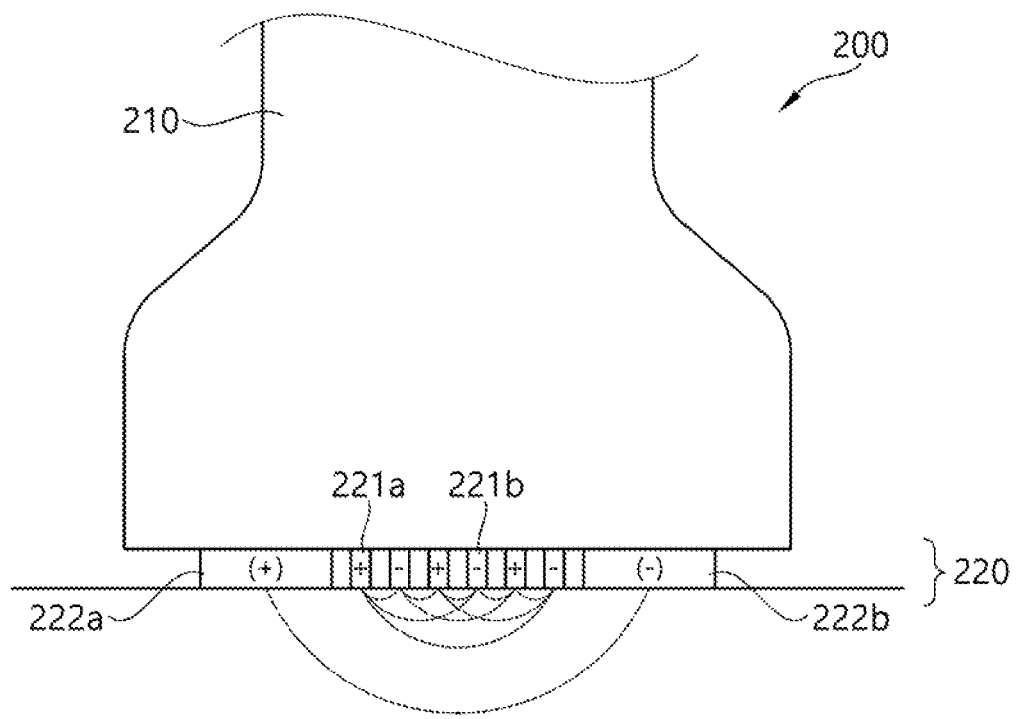
FIG. 8 is a diagram showing the state in which RF energy is transferred using the treatment method of FIG. 7.

FIG. 8 is a diagram showing the state in which RF energy is transferred using the treatment method of FIG. 7. As shown in FIG. 8, the first electrode module 221 having a relatively narrow interval between the electrodes transfers RF energy along a path of a shallow depth from a skin surface. The second electrode module 222 and the third electrode module (not shown) having a relatively wide interval between the electrodes transfer RF energy along a path of a deep depth from the skin surface. Through such a method, RF energy is transferred to a constant depth including a skin surface, so treatment is performed on a skin lesion.

When treatment at a first location is completed through the aforementioned steps, the user performs treatment by repeating the aforementioned steps while changing the treatment location.

Figure 9:
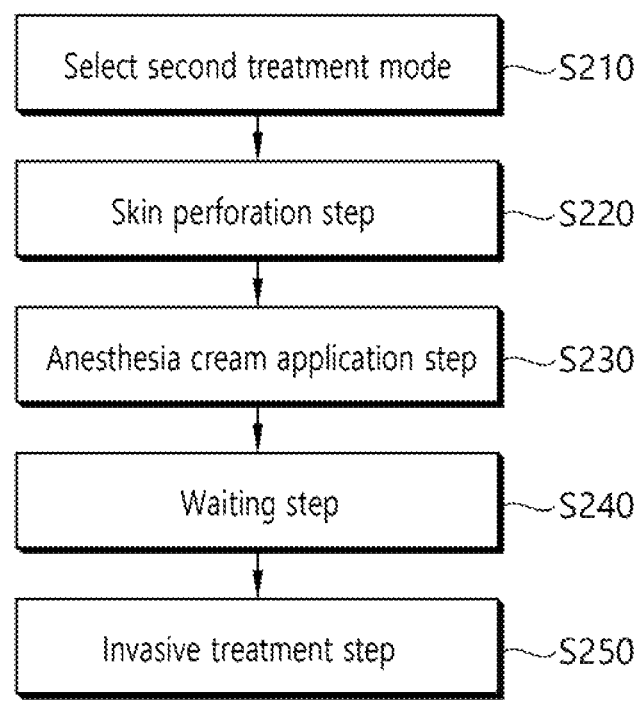
FIG. 9 is a flowchart showing treatment steps using a second treatment method.
Figure 10A:
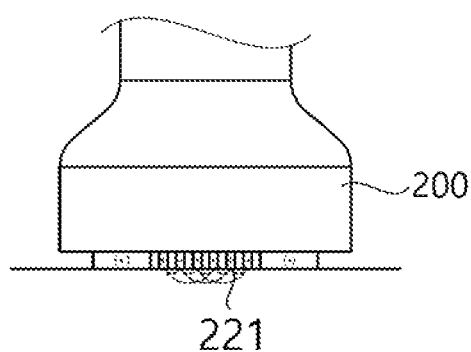
FIG. 10A to 10D are diagrams showing major steps of FIG. 9.
Figure 10B:
Figure 10C:
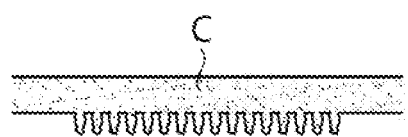
Figure 10D:
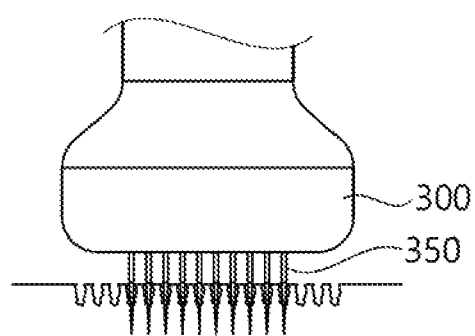

FIG. 9 is a flowchart showing treatment steps using a second treatment method. FIG. 10A to FIG. 10D are diagrams showing major steps of FIG. 9. The second treatment method is a treatment mode performed using a method of transferring RF energy to the inside of the skin. The second treatment method is applied to treatment for skin elasticity improvement and deep wrinkle improvement by directly transferring energy to the collagen layer. In this treatment method, treatment is performed using the second handpiece 300 whose electrodes can be inserted into the inside of the skin.

In the second treatment method, a patient may suffer great pain in the process of inserting the micro needles into the skin. Accordingly, in order to alleviate the pain, in general, treatment is performed in the state in which the skin has been anesthetized prior to invasive treatment. The skin anesthesia includes applying anesthesia cream to a skin surface and waiting for about 0.5 to 1 hour. A conventional anesthesia method has disadvantages in that anesthesia is not sufficiently performed up to the inside of a skin tissue and the time taken for anesthesia is long because an anesthesia component is penetrated through the skin surface. Accordingly, in an embodiment of the present invention, prior to invasive treatment, after perforations "h" are formed in a skin surface, anesthesia cream "c" may be applied. In the present embodiment, after perforations are formed in a skin surface using the first handpiece 200 for transferring RF energy to the skin surface using the contact method, skin anesthesia may be performed. When the anesthesia is effectively performed, treatment may be performed by transferring RF energy to the inside of the skin using the second handpiece 300. Accordingly, there are advantages in that anesthesia can be effectively performed up to the inside of the skin tissue using a small amount of anesthesia cream and the time can be reduced because sufficient anesthesia can be performed after a standby time of approximately 10 minutes to 15 minutes after the anesthesia cream is applied. In this embodiment, an example in which anesthesia cream is applied after perforation for effective infiltration and absorption is described. However, the present invention is not limited thereto, and other various agent such as therapeutic substance, material including stem cells or material including collagen can be applied after perforation for improving infiltration or abruption. Hereinafter, the steps are described in detail with reference to FIGS. 9 and 10.

As shown in FIG. 9, a user selects the second treatment mode using the control panel (S210). This treatment mode includes the steps of perforating the skin using the first handpiece (S220), waiting (S240) after applying anesthesia cream (S230), and performing treatment using the second handpiece 300 (S250). Accordingly, the controller may control the elements of the treatment apparatus depending on operation contents of each step.

When the user sets the treatment mode, first, the step of perforating the skin is performed (S220). As described above, the step of perforating the skin is performed using the first handpiece 200 having the contact type electrodes. The user positions the first electrode unit 220 of the first handpiece on a skin surface corresponding to a treatment location. Furthermore, the user may form perforations "h" in the skin by transferring RF energy to the skin surface through a manipulation of the first manipulation unit 211 (refer to FIGS. 10a and 10b).

This step is similar to the first treatment mode of FIG. 7 in that it is performed in such a way as to transmit RF energy to the skin surface using the first handpiece. In this case, the first treatment mode of FIG. 7 is a mode in which a lesion is directly treated using the first handpiece. In contrast, this step is different from the first treatment mode of FIG. 7 in that it is a preliminary task prior to real treatment for forming perforations in the skin in order to improve anesthesia cream penetration. Accordingly, the controller 160 may control the operation of the first handpiece differently from the first treatment mode.

Specifically, the controller 160 transfers RF energy through the first electrode module 221 so that perforations can be formed at portions where the first electrode module 221 of the first electrode unit 220 touches the skin. Furthermore, the controller 160 may control the second electrode module 222 and the third electrode module 223 to not transfer RF energy to a skin surface (refer to FIG. 10A) or to transmit only relatively small RF energy to the skin surface compared to the first treatment mode (e.g., RF energy transferred through the second electrode module and the third electrode module may be 50% or less of RF energy transferred through the same path in the first treatment mode).

Figure 11A:
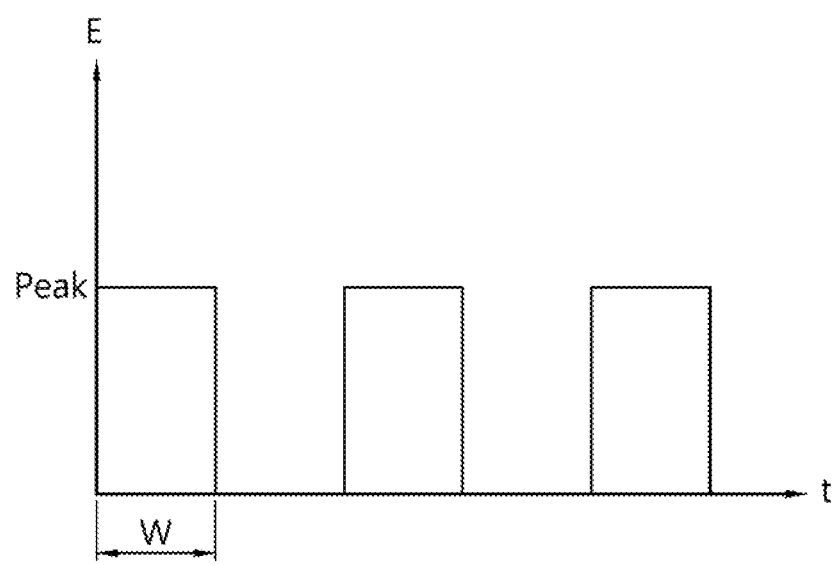
FIGS. 11A and 11B are diagrams showing the parameters of the RF energy transferred through a first electrode module.
Figure 11B:
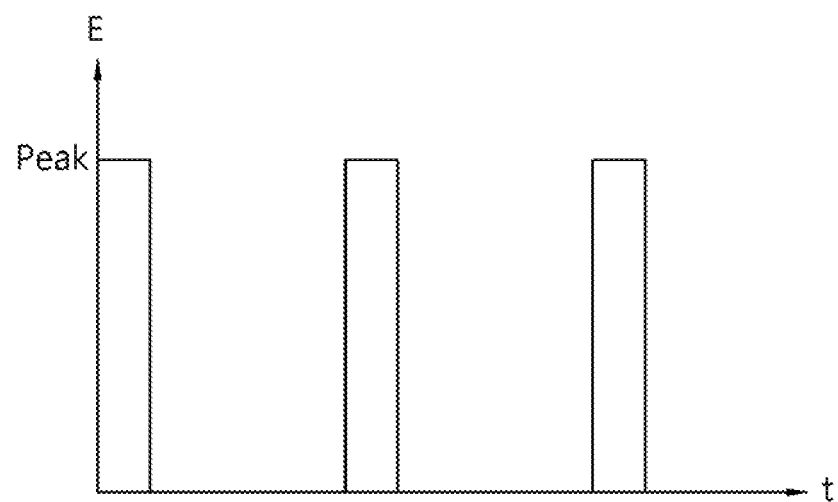

Furthermore, the controller 160 may control the parameters of the RF energy, transferred through the first electrode module 221, differently from those of the first treatment mode. FIG. 11A and FIG. 11B are diagrams showing the parameters of the RF energy transferred through the first electrode module. Specifically, FIG. 11A shows the parameters of RF energy in the first treatment mode. FIG. 11B shows the parameters of RF energy in this step. As shown in FIGS. 11A and 11B, in this step, an RF energy pulse transferred through the first electrode module has a relatively great peak value "Peak" compared to the first treatment mode and has a relatively short pulse width "W." That is, in this step, great RF energy is applied to the skin surface for a short time to break down the horny layer, thereby forming the perforations. Specifically, in this step, the peak value of the RF energy pulse is 1.5 times or more of a peak value in the first treatment mode, and the pulse width may be 0.5 or less of the peak value of the first treatment mode.

In this step, the parameters of the RF energy transferred through the first handpiece may be different controlled depending on the contents of subsequent invasive treatment. For example, if invasive treatment contents set by a user have strong strength (e.g., if the insertion depth of the second electrode unit of the second handpiece is deep or the output of RF energy transferred through the second electrode unit is large), the controller 160 may control to provide RF energy of relatively high output when the skin is perforated. Accordingly, anesthesia can be performed more easily because skin perforations are formed greatly and deep, and thus a patient's pain attributable to invasive treatment using high intensity can be reduced.

Furthermore, the controller 160 may determine whether perforations have been formed in the skin in such a way as to measure impedance of a skin surface, and may determine the end time of this step. The measurement of impedance of the skin surface may be performed using the first sensor of the first handpiece or a circuit for providing RF energy to the first electrode module. If the measured impedance value suddenly changes (e.g., if the impedance value suddenly rises), the controller 160 may determine that the perforations have been formed in the skin surface and terminate the transmission of the RF energy through the first handpiece. In addition, this step may be performed in such a way as to transmit RF energy for a preset time and to terminate the transmission of the RF energy.

When the perforations are formed in the skin surface through the aforementioned step, the step S230 of applying anesthesia cream and the step S240 of waiting for a specific time are performed. The step S230 of applying the anesthesia cream is performed in such a manner that a user directly applies the anesthesia cream "c" to the skin surface in which the perforations have been formed (refer to FIG. 10C). Furthermore, the step S240 of waiting while anesthesia is performed is performed for about 10 minutes to 15 minutes. In this case, the controller 160 may be configured to measure the standby time and to notify the user of the end time of the standby time. The time when the controller counts the standby time may be the time when the step of forming the perforations in the skin surface is terminated (i.e., the time when the driving of the first handpiece is terminated) or may be the time set by the user after the user applied the anesthesia cream. When a set standby time elapses after the counting time, the controller 160 may notify the user that the standby step has been terminated so the user can perform a subsequent invasive treatment step.

When the anesthesia of the skin surface is completed through the step, the invasive treatment step is performed (S250). In order to perform this step, the user first removes the anesthesia cream remained in the skin surface and positions the end of the second handpiece 300 on the skin surface on which the anesthesia has been completed. Furthermore, the user may insert the second electrode unit 350 including the micro needles into the inside of the skin through the skin surface by manipulating the second manipulation unit of the second handpiece 300, and may transmit RF energy to the inside of the skin (refer to FIG. 10D). In this case, the depth that the second electrode unit 350 is inserted and parameters of the RF energy transferred to the inside of the skin are controlled based on a treatment mode set by the user and information sensed by the second sensor.

When invasive treatment for a corresponding location is completed, the user may perform the invasive treatment by changing the treatment location. In this case, in the step of perforating the skin, the perforations have been performed on a plurality of spot locations on which invasive treatment is performed and thus anesthesia has been performed. Accordingly, the treatment location may change into another location on which anesthesia has been performed and the invasive treatment may be repeatedly performed.

The second treatment method of treating a lesion in an invasive manner using the second handpiece has been described above. In this case, in an embodiment of the present invention, skin perforations can be performed using the contact type handpiece by taking advantages of the single treatment apparatus including the contact type handpiece and the invasive type handpiece, and anesthesia may be performed. In this case, there are advantages in that an anesthesia effect can be improved, the time taken for anesthesia can be reduced, a patient's pain can be alleviated, and treatment can be rapidly performed.

In accordance with the embodiments of the present invention, there is an advantage in that a treatment effect can be improved because the contact type handpiece and the invasive type handpiece are used in combination. Specifically, there are effects in that an anesthesia effect can be rapidly obtained using a very small amount and the treatment time can be reduced because paths through which an anesthetic material can penetrate are formed using the contact type handpiece.

The treatment apparatus for performing treatment by transferring RF energy to a skin tissue has been chiefly described above. This is an example and may be applied to a treatment apparatus focused on other tissue not a skin tissue. Furthermore, the treatment apparatus including the main body and the handpiece has been chiefly described, but the present invention is not limited thereto and may be applied to a treatment apparatus in which the handpiece is configured in a single module form.

Although the embodiments of the present invention have been described in detail, the present invention is not limited to the embodiment. It is to be noted that a person having ordinary skill in the art to which the present invention pertains may modify or change the present invention in various manners without departing from the scope of the technical characteristics of the present invention defined in the claims.

What is claimed is:

1. A skin treatment method using radio frequency (RF) wave energy, comprising:
   a perforation forming step of forming perforations in a skin surface by transferring RF energy to the skin surface using a first handpiece comprising a first electrode unit coming into contact with the skin surface;
   a step of applying an agent to the skin surface in which the perforations have been formed; and
   a treatment step of treating the skin by transferring RF energy to an inside of the skin into which the agent has penetrated using a second handpiece comprising a second electrode unit inserted into the inside of the skin.

2. The skin treatment method of claim 1, wherein the applied agent comprises an anesthesia component to alleviate pain occurring when the second electrode unit is inserted into the inside of the skin in the treatment step.

3. The skin treatment method of claim 1, wherein:
   the first handpiece selectively operates in a first mode in which the perforation forming step is performed or a second mode in which a lesion is treated by transferring energy to the skin surface without forming perforations in the skin surface, and
   an RF energy waveform of the first mode has a larger peak power value or shorter pulse width than an RF energy waveform of the second mode.

4. The skin treatment method of claim 1, further comprising a step of setting a mode of the treatment step prior to the perforation forming step,
   wherein in the perforation forming step, parameters of the RF energy transferred through the first electrode unit are differently controlled depending on a set mode of the treatment step.

5. The skin treatment method of claim 1, wherein:
   the treatment step is performed after waiting for a specific time after the agent is applied,
   the treatment step comprises a notification step of notifying an operator of a treatment time of the treatment step, and
   the notification step comprises providing a notification signal to the operator when a preset time elapses from an end time of the perforation forming step, an end time of the step of applying the agent, or a time set by the operator.

6. The skin treatment method of claim 1, wherein a controller senses impedance of the skin surface during the perforation forming step and controls the transfer of the RF energy through the first electrode unit based on a change in characteristics of the impedance.

7. The skin treatment method of claim 6, wherein the controller terminates the transfer of the RF energy through the first electrode unit when the impedance of the skin surface suddenly rises during the perforation forming step.

* * * * *